United States Patent [19]

Mahailet et al.

[11] Patent Number: 4,483,852

[45] Date of Patent: Nov. 20, 1984

[54] **PHARMACEUTICAL COMPOSITIONS CONTAINING A FRACTION EXTRACTED FROM MANDASSI (*CYPERUS ARTICULATUS L.*)**

[75] Inventors: Jean B. Mahailet, Bondy; Jean P. Gabriel, Tours St Symphorien, both of France

[73] Assignee: Synthelabo, Paris, France

[21] Appl. No.: 433,269

[22] Filed: Oct. 7, 1982

[30] Foreign Application Priority Data

Oct. 7, 1981 [FR] France ................. 81 18891

[51] Int. Cl.$^3$ ............................................. A61K 35/78
[52] U.S. Cl. ..................................................... 424/195
[58] Field of Search ........................................ 424/195

[56] References Cited

PUBLICATIONS

Krall, et al., Epilepsia, 19: 395–407, 1978.
Krall, et al., Epilepsia, 19: 409–428, 1978.
Steinmetz, Codex Vegetabilis No. 382, 383, 1957.
Universal Herbal or, Botanical, Medical and Agri. Dictionary, p. 422, No. 1, 1823.
L. S. Goodman et al., J. Pharm. Expt. Ther. 108: 168–176, 1953.

*Primary Examiner*—Albert T. Meyers
*Assistant Examiner*—John W. Rollins, Jr.
*Attorney, Agent, or Firm*—Wegner & Bretschneider

[57] ABSTRACT

From the roots of the plant Mandassi (*Cyperus articulatus L.*) a fraction is extracted which is therapeutically useful, more particularly as an anticonvulsant.

3 Claims, No Drawings

PHARMACEUTICAL COMPOSITIONS CONTAINING A FRACTION EXTRACTED FROM MANDASSI (*CYPERUS ARTICULATUS L.*)

The present invention relates to the application in therapy of a fraction extracted from Mandassi (*Cyperus articulatus L.*) and to a process for extraction of this fraction.

Mandassi, or *Cyperus articulatus L.*, is a plant with an odoriferous underground stock and a cylindrical floriferous aerial stem, which grows in Africa, in particular in the following countries: Mauritania, Senegal, Mali, Guinea, Liberia, the Ivory Coast, the Congo, the Upper Volta, Ghana, Togo, Nigeria and the Cameroons.

It has now unexpectedly been found that from the Mandassi roots it is possible to extract a therapeutically useful fraction which is active in the field of the central nervous system, in particular as an anticonvulsant.

According to the invention, the therapeutically active fraction is extracted from the Mandassi roots by a process characterised in that rhizomes of Mandassi (*Cyperus articulatus L.*) are ground and extracted with water, preferably by decoction using, for example, 10 times their weight of water, the solution obtained is concentrated, preferably until its weight is substantially equal to the weight of the plant rhizomes used, 95% alcohol is poured into the concentrate and the precipitate formed is isolated, purified and dried.

A particular method for carrying out the process for extraction of the active fraction is as follows:

500 grams of dry rhizomes of Mandassi originating from the Cameroons are ground and extracted, by decoction for 2 hours, with 10 times their weight of water.

The resulting solution is drawn off and filtered hot, and the filtrate is then concentrated in vacuo until its weight is equal to the weight of the plant used.

Twice the weight by volume of 95% alcohol, that is to say 1 liter, is then poured in with stirring.

The reaction mixture is left to stand and the precipitate is then isolated on a Büchner filter. The undried precipitate which has been filtered off is taken up in 70% alcohol until the alcohol phase shows no coloration. The precipitate must be taken up about 10 times with 100 ml of alcohol each time.

The alcohol phases are then concentrated in vacuo until no distillation takes place.

The residue is taken up twice in 100 ml of 70% alcohol, with filtration between the two operations.

The insoluble material is dried in vacuo and constitutes the active fraction. 5.5 g of active fraction are obtained.

This active fraction is in the form of a greyish-white powder which is soluble in water and in 65% alcohol.

The anticonvulsant activity of the fraction extracted in this way from Mandassi roots was studied in respect of the convulsions induced by Cardiazol.

The experimental procedure is as follows:

Mice receive the solution of the product to be tested, or the solvent, by intraperitoneal administration 30 minutes before the injection of the convulsant and in an amount of 20 ml/kg. The solvent is a 1% strength solution of Tween 80 in distilled water.

The Cardiazol is injected intravenously at a dose of 35 mg/kg in physiological serum, in an amount of 10 ml/kg.

The animals are then placed in individual cages made of Makrolon and observed for 1 hour.

For each batch of 10 mice, the percentage of mice showing clonic convulsions is recorded and the percentage protection relative to the control batch is then calculated.

The fraction extracted from Mandassi is dissolved at various concentrations in the solvent.

The following Table gives the results expressed as percentage protection.

TABLE

| Fraction in solution (dose g/kg) | % Protection |
|---|---|
| 0.315 | 86 |
| 0.158 | 88 |
| 0.079 | 77 |
| 0.039 | 29 |
| 0.017 | 29 |

The results show that the Mandassi fraction extracted by the process of the invention is active as an anticonvulsant and can be used for the treatment of epilepsy.

The invention also includes the pharmaceutical compositions containing the active fraction extracted from Mandassi as the active principle, in association with any pharmaceutically-acceptable excipient suitable for oral or parenteral administration.

The customary forms suitable for oral or parenteral administration can be used, such as tablets, coated tablets, gelatin capsules, capsules, cachets, solutions or suspensions to be taken orally, or injectable solutions.

We claim:

1. A process for the isolation of a fraction of Mandassi (*Cyperus articulatus L.*) active as an anti-convulsant which comprises the steps:
    (a) extracting ground Mandassi rhizomes by decoction with water,
    (b) hot filtering the aqueous extract,
    (c) concentrating the aqueous extract until its weight is substantially equal to the weight of rhizomes initially extracted,
    (d) adding twice the weight by volume of 95% alcohol to the concentrated extract, and
    (e) separating the solid material which precipitates on addition of the alcohol.

2. The product made by the process of claim 1.

3. A pharmaceutical composition in unit dosage form containing an anti-convulsant amount of the product of claim 1 in association with a suitable excipient.

* * * * *